United States Patent
Sung (10) Patent No.: US 11,456,060 B1
(45) Date of Patent: Sep. 27, 2022

(54) APPARATUS AND METHOD AND FOR CALIBRATING ANALYTE DATA

(71) Applicant: SB Solutions Inc., Ulsan (KR)

(72) Inventor: Namhwan Sung, Ulsan (KR)

(73) Assignee: SB Solutions Inc., Ulsan (KR)

( * ) Notice: Subject to any disclaimer, the term of this patent is extended or adjusted under 35 U.S.C. 154(b) by 0 days.

(21) Appl. No.: 17/399,924

(22) Filed: Aug. 11, 2021

(30) Foreign Application Priority Data

May 18, 2021 (KR) .................. 10-2021-0063885

(51) Int. Cl.
*G16C 20/70* (2019.01)
*G06N 3/04* (2006.01)

(52) U.S. Cl.
CPC ........... *G16C 20/70* (2019.02); *G06N 3/0472* (2013.01)

(58) Field of Classification Search
CPC ............................. G16C 20/70; G06N 3/0472
See application file for complete search history.

(56) References Cited

U.S. PATENT DOCUMENTS

| | | | |
|---|---|---|---|
| 8,224,415 B2* | 7/2012 | Budiman | G16H 10/40 600/347 |
| 8,478,557 B2* | 7/2013 | Hayter | A61M 5/1723 702/104 |
| 2014/0121480 A1* | 5/2014 | Budiman | G16H 40/40 600/309 |
| 2014/0278189 A1* | 9/2014 | Vanslyke | A61B 5/1495 702/104 |
| 2015/0205000 A1* | 7/2015 | Perkins | G01V 8/10 702/8 |
| 2017/0074757 A1* | 3/2017 | Garcia | A61B 5/0031 |
| 2021/0298648 A1* | 9/2021 | Hefner | A61B 5/14532 |

* cited by examiner

*Primary Examiner* — Raymond L Nimox
(74) *Attorney, Agent, or Firm* — Christensen O'Connor Johnson Kindness PLLC

(57) ABSTRACT

Disclosed are an apparatus and method for calibrating analyte data. In an embodiment, a method of calibrating analyte data may include receiving first analyte data measured by a reference device, storing the received first analyte, calculating a calibration value by using an artificial intelligence (AI) calibration model having second analyte data measured by an analyte sensor and the stored first analyte data as inputs, and calculating the final analyte data by incorporating the calculated calibration value into the second analyte data.

14 Claims, 6 Drawing Sheets

APPARATUS AND METHOD AND FOR CALIBRATING ANALYTE DATA

CROSS-REFERENCES TO RELATED APPLICATIONS

This application is based on and claims priority under 35 U.S.C. 119 to Korean Patent Application No. 10-2021-0063885, filed on May 18, 2021, in the Korean intellectual property office, the disclosures of which are herein incorporated by reference in their entireties.

TECHNICAL FIELD

The following description relates to an apparatus and method for calibrating analyte data.

BACKGROUND OF THE INVENTION

In an analyte sensor for measuring a concentration of an analyte, the accuracy of measurement is reduced due to a change in the surrounding environment or over time. In order to supplement such a problem, an apparatus for calibrating output data of the analyte sensor is used. The apparatus for calibrating analyte data is an essential element for maintaining the accuracy of the analyte sensor by calibrating an error of a measured value attributable to an environment factor, such as a temperature or humidity, a temporal factor, such as the deterioration of the sensor.

However, a conventional calibration apparatus has accurate measurement results at calibration timing because a simple mapping table or a linear function is used, but has a problem in that a measurement error is increased over time. For this reason, in the conventional calibration apparatus, measurement results need to be periodically calibrated.

SUMMARY

This summary is provided to introduce a selection of concepts in a simplified form that are further described below in the Detailed Description. This summary is not intended to identify key characteristics of the claimed subject matter, nor is it intended to be used as an aid in determining the scope of the claimed subject matter.

The present disclosure provides an apparatus and method for calibrating analyte data, which can minimize a calibration error according to the lapse of time and increase a calibration cycle by predicting a calibration value attributable to a temporal change through a calibration value prediction model implemented as a non-linear model.

In an aspect, there is provided a method of calibrating, by a computer device including at least one processor, analyte data, including receiving, by the at least one processor, first analyte data measured by a reference device, storing, by the at least one processor, the received first analyte, calculating, by the at least one processor, a calibration value by using an artificial intelligence (AI) calibration model having second analyte data measured by an analyte sensor and the stored first analyte data as inputs, and calculating, by the at least one processor, final analyte data by incorporating the calculated calibration value into the second analyte data.

According to an aspect, calculating the calibration value may include calculating, as the calibration value, an average of probability distributions of output nodes included in a neural network of the AI calibration model.

According to another aspect, calculating the calibration value may include further computing prediction uncertainty for determining time when the first analyte data is received again by using the AI calibration model having the second analyte data and the stored first analyte data as inputs.

According to yet another aspect, the prediction uncertainty may include dispersion of the probability distributions of the output nodes included in the neural network of the AI calibration model.

According to yet another aspect, the method of calibrating analyte data may further include comparing, by the at least one processor, the prediction uncertainty with a preset threshold value, generating, by the at least one processor, a calibration request signal when the prediction uncertainty is equal to or greater than the preset threshold value, and outputting, by the at least one processor, the generated calibration request signal.

According to yet another aspect, calculating the final analyte data may include calculating the final analyte data when the prediction uncertainty is smaller than the preset threshold value.

According to yet another aspect, the calibration request signal may include a signal for requesting the re-measurement and re-reception of the first analyte data.

According to yet another aspect, the second analyte data may include data obtained by accumulating analyte data measured by the analyte sensor for a given time.

In an aspect, there is provided a method of calibrating, by a computer device including at least one processor, analyte data, including receiving, by the at least one processor, first analyte data measured by a reference device, storing, by the at least one processor, the received first analyte, and calculating, by the at least one processor, calibrated second analyte data by using an artificial intelligence (AI) calibration model having second analyte data measured by an analyte sensor and the stored first analyte data as inputs.

In an aspect, there is provided a computer device including at least one processor implemented to execute a computer-readable instruction. The at least one processor is configured to receive first analyte data measured by a reference device, store the received first analyte, calculate a calibration value by using an artificial intelligence (AI) calibration model having second analyte data measured by an analyte sensor and the stored first analyte data as inputs, and calculate final analyte data by incorporating the calculated calibration value into the second analyte data.

In an aspect, there is provided a computer device including at least one processor implemented to execute a computer-readable instruction. The at least one processor is configured to receive first analyte data measured by a reference device, store the received first analyte data, and calculate calibrated second analyte data by using an artificial intelligence (AI) calibration model having second analyte data measured by an analyte sensor and the stored first analyte data as inputs.

A calibration cycle can be increased by reducing a calibration error according to the lapse of time because a simple measurement difference at calibration timing is not used as a calibration value, but a result obtained by inputting the measurement difference into the calibration value prediction model is used as a calibration value.

Furthermore, the reliability of a currently predicted calibration value can be evaluated using the calibration value prediction model that outputs prediction uncertainty. Necessity for calibration can be determined based on the evaluation. Accordingly, unnecessary calibration can be avoided, and a user can be requested to immediately perform a calibration procedure regardless of a calibration cycle when calibration is necessary.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessive unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the gist of the embodiment unnecessarily vague.

Furthermore, in describing components of an embodiments, terms, such as a first, a second, A, B, (a), and (b), may be used. Such terms are used only to distinguish one component from the other component, and the essence, order, or sequence of a corresponding component is not limited by the terms. When it is said that one component is "connected", "combined", or "coupled" to the other component, the one component may be directly connected or coupled to the other component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

A system for predicting a health risk according to embodiments of the present disclosure may be implemented by at least one computer device. In this case, a computer program according to an embodiment of the present disclosure may be installed and driven in the computer device. The computer device may perform a method of predicting a health risk according to embodiments of the present disclosure under the control of the driven computer program. The aforementioned computer program may be stored in a computer-readable recording medium in order to execute the method of predicting a health risk by being coupled to the computer device.

Figure 1:
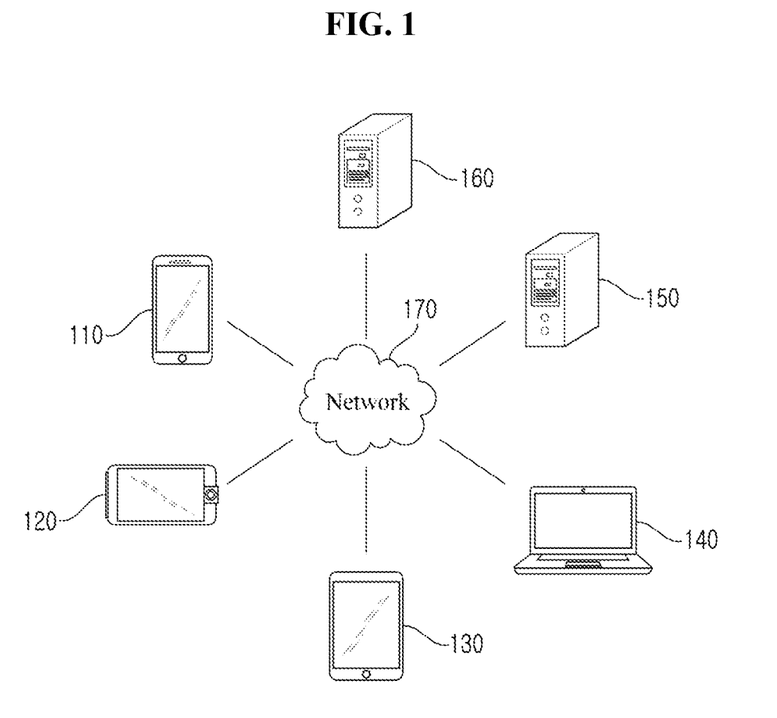
FIG. 1 is a diagram illustrating an example of a network environment according to an embodiment of the present disclosure.

FIG. 1 is a diagram illustrating an example of a network environment according to an embodiment of the present disclosure. The network environment of FIG. 1 illustrates an example including a plurality of electronic devices 110, 120, 130, and 140, a plurality of servers 150 and 160, and a network 170. FIG. 1 is an example for describing the present disclosure, and the number of electronic devices or the number of servers is not limited to that of FIG. 1. Furthermore, the network environment of FIG. 1 merely describes one of environments applicable to the present embodiments, and an environment applicable to the present embodiments is not limited to the network environment of FIG. 1.

Each of the plurality of electronic devices 110, 120, 130 and 140 may be a stationary terminal or a mobile terminal implemented as a computer device. For example, the plurality of electronic devices 110, 120, 130 and 140 may include a smartphone, a mobile phone, a navigation device, a computer, a laptop computer, a device for digital broadcasting, personal digital assistants (PDA), a portable multimedia player (PMP), a tablet PC, etc. For example, in FIG. 1, a shape of a smartphone is illustrated as being an example of the electronic device 110. However, in embodiments of the present disclosure, the electronic device 110 may mean one of various physical computer devices capable of communicating with other electronic devices 120, 130 and 140 and/or the servers 150 and 160 over the network 170 substantially using a wireless or wired communication method.

The communication method is not limited, and may include short-distance wireless communication between devices in addition to communication methods using communication networks (e.g., a mobile communication network, wired Internet, wireless Internet, and a broadcasting network) which may be included in the network 170. For example, the network 170 may include one or more given networks of a personal area network (PAN), a local area network (LAN), a campus area network (CAN), a metropolitan area network (MAN), a wide area network (WAN), a broadband network (BBN), and the Internet. Furthermore, the network 170 may include one or more of network topologies, including a bus network, a star network, a ring network, a mesh network, a star-bus network, and a tree or hierarchical network, but is not limited thereto.

Each of the servers 150 and 160 may be implemented as a computer device or a plurality of computer devices, which provides an instruction, a code, a file, content, or a service through communication with the plurality of electronic devices 110, 120, 130 and 140 over the network 170. For example, the server 150 may be a system that provides the plurality of electronic devices 110, 120, 130, and 140 with services (e.g., a health management service, an instant messaging service, a financial service, a game service, a group call service (or voice conference service), a messaging service, a mailing service, a social network service, a map service, a translation service, a payment service, a search service, and a content provision service).

Figure 2:
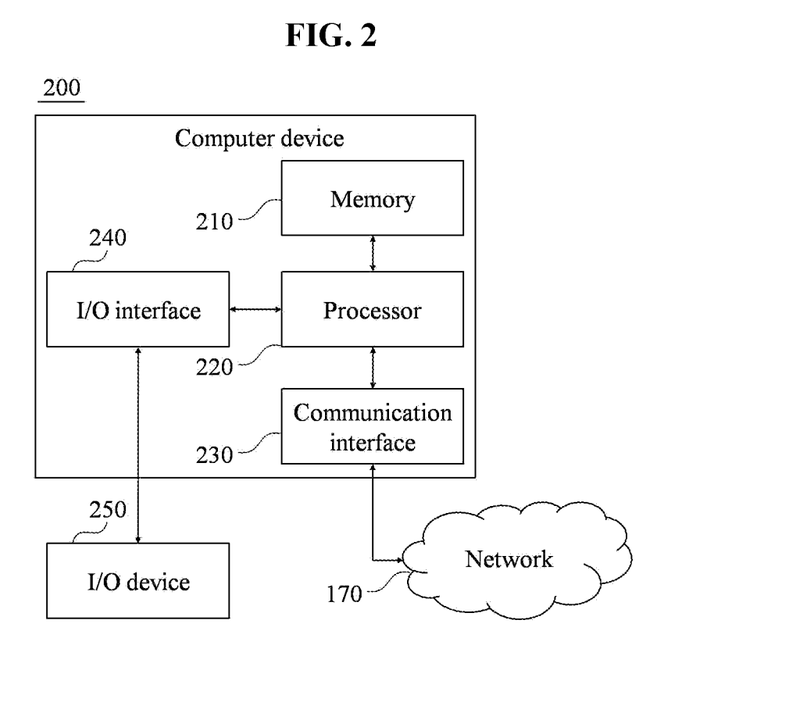
FIG. 2 is a block diagram illustrating an example of a computer device according to an embodiment of the present disclosure.

FIG. 2 is a block diagram illustrating an example of a computer device according to an embodiment of the present disclosure. Each of the plurality of electronic devices 110, 120, 130 and 140 or each of the servers 150 and 160 may be implemented as a computer device 200 illustrated in FIG. 2.

As illustrated in FIG. 2, the computer device 200 may include a memory 210, a processor 220, a communication interface 230 and an input/output (I/O) interface 240. The memory 210 is a computer-readable medium, and may include permanent mass storage devices, such as a random access memory (RAM), a read only memory (ROM) and a disk drive. In this case, the permanent mass storage device, such as a ROM and a disk drive, may be included in the computer device 200 as a permanent storage device separated from the memory 210. Furthermore, an operating system and at least one program code may be stored in the memory 210. Such software components may be loaded from a computer-readable medium, separated from the memory 210, to the memory 210. Such a separate computer-readable medium may include computer-readable recording media, such as a floppy drive, a disk, a tape, a DVD/CD-ROM drive, and a memory card. In another embodiment, software components may be loaded onto the memory 210 through the communication interface 230 not a computer-readable medium. For example, the software components may be loaded onto the memory 210 of the computer device 200 based on a computer program installed by files received over the network 170.

The processor 220 may be configured to process instructions of a computer program by performing basic arithmetic, logic and input/output (I/O) operations. The instructions may be provided to the processor 220 by the memory 210 or the communication interface 230. For example, the processor 220 may be configured to execute received instructions based on a program code stored in a recording device, such as the memory 210.

The communication interface 230 may provide a function for enabling the computer device 200 to communicate with other devices (e.g., the aforementioned storage devices) over the network 170. For example, a request, a command, data or a file generated by the processor 220 of the computer device 200 based on a program code stored in a recording device, such as the memory 210, may be provided to other devices over the network 170 under the control of the communication interface 230. Inversely, a signal, a command, data or a file from another device may be received by the computer device 200 through the communication interface 230 of the computer device 200 over the network 170. A signal, a command or a file received through the communication interface 230 may be transmitted to the processor 220 or the memory 210. A file received through the communication interface 230 may be stored in a storage device (e.g., the aforementioned permanent storage device) which may be further included in the computer device 200.

The I/O interface 240 may be means for an interface with an I/O device 250. For example, the input device may include a device, such as a microphone, a keyboard, or a mouse. The output device may include a device, such as a display or a speaker. For another example, the I/O interface 240 may be means for an interface with a device in which functions for input and output have been integrated into one, such as a touch screen. At least one of the I/O devices 250, together with the computer device 200, may be configured as a single device. For example, the I/O device may be implemented in a form in which a touch screen, a microphone, a speaker, etc. are included in the computer device 200 like a smartphone.

Furthermore, in other embodiments, the computer device 200 may include components greater or smaller than the components of FIG. 2. However, it is not necessary to clearly illustrate most of conventional components. For example, the computer device 200 may be implemented to include at least some of the I/O devices 250 or may further include other components, such as a transceiver and a database.

Figure 3:
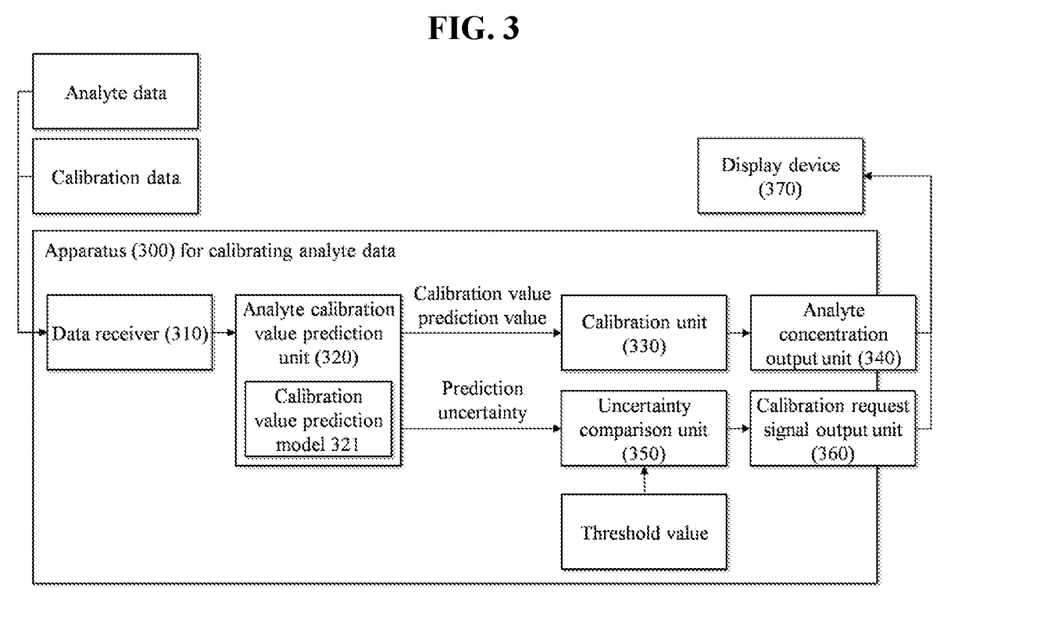
FIG. 3 is a diagram illustrating an example of an apparatus for calibrating analyte data according to an embodiment of the present disclosure.

FIG. 3 is a diagram illustrating an example of an apparatus for calibrating analyte data according to an embodiment of the present disclosure. As illustrated in FIG. 3, the apparatus 300 for calibrating analyte data according to the present disclosure may include a data receiver 310, an analyte calibration value prediction unit 320, a calibration unit 330, an analyte concentration output unit 340, an uncertainty comparison unit 350 and a calibration request signal output unit 360.

The data receiver 310 may receive analyte data measured by an analyte sensor and a reference device. In this case, the reference device may be a sensor device capable of precisely measuring analyte data. Such analyte data measured by the reference device may be used as calibration data for calibrating analyte data measured by the analyte sensor. Furthermore, the analyte data may include a value of a concentration of an analyte, such as blood glucose or oxygen saturation, or may include a numerical value on which a value of a concentration of an analyte can be calculated or estimated. If analyte data includes a numerical value on which a value of a concentration of an analyte can be calculated or estimated, the apparatus 300 for calibrating analyte data or the data receiver 310 may calculate or estimate the value of a concentration of the analyte from the analyte data. When analyte data measured by the reference device is received once as calibration data, the analyte data may be stored and used again in the apparatus 300 for calibrating analyte data. Subsequently, when a calibration request signal is generated and output by the apparatus 300 for calibrating analyte data, analyte data measured by the reference device may be received again by the apparatus 300 for calibrating analyte data as new calibration data.

The analyte sensor may be a device for generating and providing analyte data. The analyte sensor may transmit, to the apparatus 300 for calibrating analyte data, analyte data measured by the analyte sensor through communication with the apparatus 300 for calibrating analyte data. In some embodiments, the analyte sensor may be included in the apparatus 300 for calibrating analyte data, or the analyte sensor may include the apparatus 300 for calibrating analyte data. In another embodiment, the apparatus 300 for calibrating analyte data may be implemented in the form of a server or cloud for receiving and calibrating analyte data. For example, analyte data measured by the analyte sensor may be transmitted to the apparatus 300 for calibrating analyte data, implemented as a server or cloud on a network, directly from the analyte sensor or through a separate device (e.g., smartphone) communicating with the analyte sensor.

The analyte calibration value prediction unit 320 may calculate an analyte calibration value based on a concentration of an analyte, output by the data receiver 310, through a calibration value prediction model 321, and may output the calculated analyte calibration value. For example, the analyte calibration value prediction unit 320 may input, to the calibration value prediction model 321, analyte data measured by the analyte sensor and analyte data (i.e., analyte data measured by the reference device) stored as calibration data. The calibration value prediction model 321 may be trained to receive analyte data of the analyte sensor and analyte data of the reference device and to output a calibration value at current timing (or a prediction value of a calibration value at current timing).

In some embodiments, the analyte calibration value prediction unit 320 may further calculate and output prediction uncertainty based on a concentration of an analyte. A calibration value and prediction uncertainty will be more specifically described later.

After calibrating a concentration of an analyte received from the data receiver 310 by adding an analyte calibration value predicted by the analyte calibration value prediction unit 320 to the concentration of the analyte, the calibration unit 330 may transmit a value of the calibrated concentration of the analyte to the analyte concentration output unit 340.

The analyte concentration output unit 340 may output the value of a calibrated concentration of the analyte to a connected device. The connected device may be a display device 370 illustrated in FIG. 3, but the present disclosure is not limited thereto. For example, various devices for receiving and using a value of a calibrated concentration of an analyte, such as a smart device, a wearable device, or a management server, may be used as the connected device. In this case, the "connection" of the connected device may mean that data can be transmitted and received through wired or wireless communication with the apparatus 300 for calibrating analyte data. The connected device may display the received value of a concentration of the analyte on a display included in the connected device or perform a warning operation using the value of a concentration of the analyte, may secondarily process the value of a concentration of the analyte, and may transmit the processed value to another device.

The uncertainty comparison unit 350 may compare prediction uncertainty, computed by the analyte calibration value prediction unit 320, with a threshold value, may generate a calibration request signal when the prediction uncertainty is equal to or greater than the threshold value as a result of the comparison, and may transmit the calibration request signal to the calibration request signal output unit 360.

When a calibration request signal is generated by the uncertainty comparison unit 350, the calibration request signal output unit 360 may output the generated calibration request signal to the connected device. When receiving the calibration request signal, the connected device may display a message on the display or may give warning to a user by generating a sound, light, vibration, etc. Furthermore, the connected device may transmit the received calibration request signal to another device. In response to such a calibration request signal, new calibration data may be received by (or input to) the apparatus 300 for calibrating analyte data. The apparatus 300 for calibrating analyte data may calculate and use a calibration value by using analyte data input as new calibration data.

If the apparatus 300 for calibrating analyte data is implemented as the computer device 200, the components of the apparatus 300 for calibrating analyte data, described with reference to FIG. 3, may be functional expressions of an operation performed by the processor 220 of the computer device 200. For example, the data receiver 310 is used as a functional expression of an operation of receiving, by the processor 220 of the computer device 200, analyte data measured by the analyte sensor and the reference device and calculating a concentration of the analyte.

Furthermore, in the embodiment of FIG. 3, the analyte calibration value prediction unit 320 and the calibration unit 330 have been separated and described. In some embodiments, the analyte calibration value prediction unit 320 and the calibration unit 330 may be combined as one component. For example, the calibration value prediction model 321 included in the analyte calibration value prediction unit 320 may be trained to receive analyte data of the analyte sensor and analyte data of the reference device and to output calibrated analyte data. In this case, the output of the analyte calibration value prediction unit 320 may be calibrated analyte data, and the calibration unit 330 may be omitted.

Referring back to FIG. 3, the calibration value prediction model 321 of the analyte calibration value prediction unit 320 for calculating a concentration of an analyte may be implemented using at least one of various algorithm, such as multi-layer Perceptron (MLP), a deep neural network (DNN), a convolutional neural network (CNN), a recurrent neural network (RNN), a group convolutional neural network (G-CNN), a recurrent convolutional neural network (R-CNN), but the present disclosure is not limited to a specific algorithm.

Furthermore, the analyte calibration value prediction unit 320 may apply a method of adding given noise to an input variable (input perturbation) or random dropping out the inside of an artificial intelligence (AI) model in order to compute prediction uncertainty. Examples of such an algorithm includes a Bayesian neural network (BNN), Deep Ensembles, etc., but an algorithm for computing prediction uncertainty is not limited to a specific algorithm.

Figure 4:
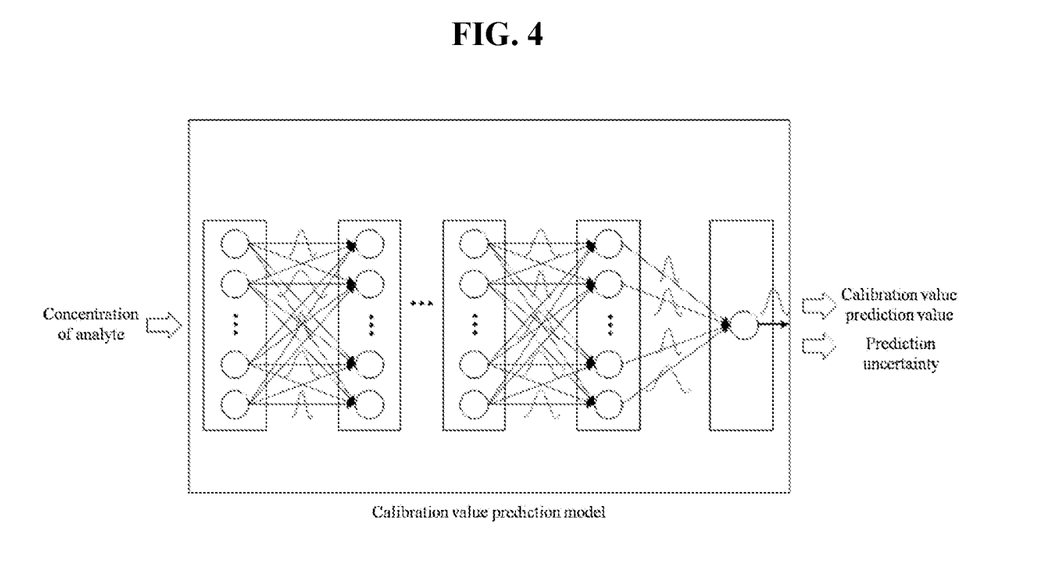
FIG. 4 is a concept view in which a calibration value prediction value and prediction uncertainty are computed by inputting a concentration of an analyte to a calibration value prediction model using a Bayesian neural network (BNN) in an embodiment of the present disclosure.

FIG. 4 is a concept view in which a calibration value prediction value and prediction uncertainty are computed by inputting a concentration of an analyte to the calibration value prediction model using the Bayesian neural network (BNN) in an embodiment of the present disclosure. The BNN is a model capable of computing an average and dispersion of the final prediction values because each of weights of a neural network consists of a probability distribution. The uncertainty of prediction can be computed using the BNN.

An input to the calibration value prediction model 321 is a concentration of an analyte measured by the analyte sensor and the reference device. In some embodiments, a concentration of an analyte measured by a plurality of analyte sensors and a reference device may be input to the calibration value prediction model 321. In the embodiment of FIG. 4, the internal neural network of the calibration value prediction model 321 may consist of the BNN. In this case, each weight has a probability distribution. Accordingly, the output of each node of the neural network may be calculated as a value having the probability distribution.

In this case, the neural network of the calibration value prediction model 321 may compute a calibration value prediction value and prediction uncertainty by using probability distributions of output nodes. An average of the probability distributions of the output nodes may be considered to be a calibration value prediction value, and dispersion of the probability distributions of the output nodes may be considered to be prediction uncertainty. It may be considered that prediction uncertainty is reduced as dispersion of the probability distributions of the output nodes becomes smaller and prediction uncertainty is increased as dispersion of the probability distributions of the output nodes becomes great.

The uncertainty comparison unit 350 may compare prediction uncertainty, that is, dispersion of probability distributions of the output nodes output by the calibration value prediction model 321, with a threshold value. The dispersion is a value in which a variable is far from an average. When the dispersion is greater than the threshold value, it may be determined that calibration is necessary. Accordingly, when dispersion output by the calibration value prediction model 321 is greater than the threshold value, the uncertainty comparison unit 350 may generate a calibration request signal. To generate and transmit the calibration request signal may include requesting the reference device to measure and transmit analyte data again. In other words, the prediction uncertainty may be used as a criterion for determining timing at which analyte data measured by the reference device is received again. The calibration request signal may include a signal for requesting the re-measurement and re-reception of analyte data through the reference device.

As described above, if a prediction uncertainty computation model such as the BNN is used, calibration necessity can be determined using prediction uncertainty.

Figure 5:
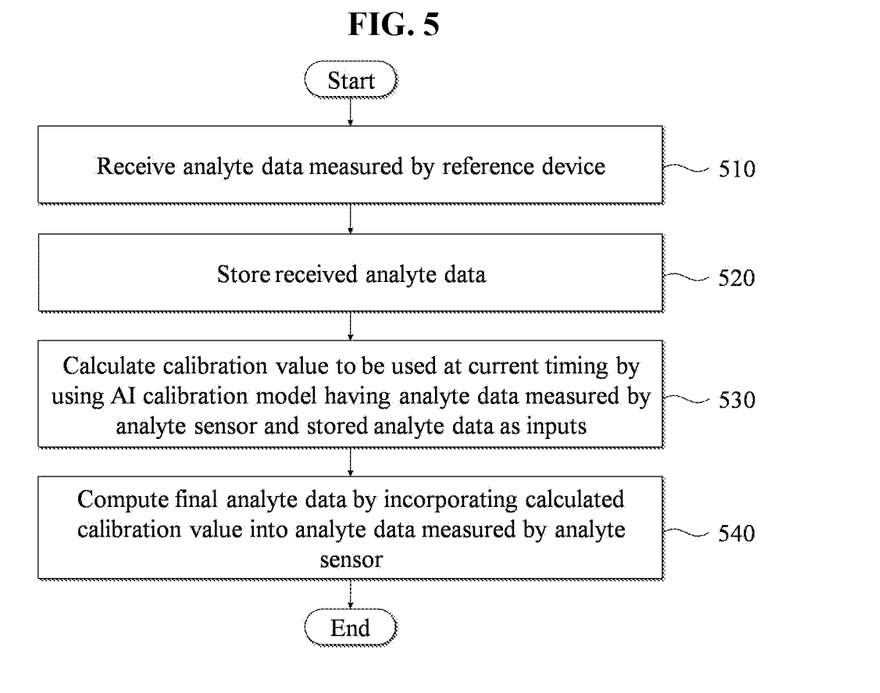
FIG. 5 is a flowchart illustrating an example of a method of calibrating analyte data according to an embodiment of the present disclosure.

FIG. 5 is a flowchart illustrating an example of a method of calibrating analyte data according to an embodiment of the present disclosure. The method of calibrating analyte data according to the present disclosure may be performed by the computer device 200 that implements the apparatus 300 for calibrating analyte data. In this case, the processor 220 of the computer device 200 may be implemented to execute a control instruction based on a code of an operating system or a code of at least one computer program, which is included in the memory 210. In this case, the processor 220 may control the computer device 200 so that the computer device 200 performs steps 510 to 550 included in the method of FIG. 5 in response to a control instruction provided by a code stored in the computer device 200.

In step 510, the computer device 200 may receive analyte data measured by the reference device. In this case, the analyte data measured by the reference device may be received from a separate device through the communication interface 230, but may be received through the I/O interface 240. In this case, the "reception" may mean that data is input to the computer device 200 through the communication interface 230 or the I/O interface 240 under the control of the processor 220 of the computer device 200. The analyte data may include a value of a concentration of an analyte or may include a numerical value on which a value of a concentration of an analyte may be calculated or estimated.

In step 520, the computer device 200 may store the received analyte data. For example, the computer device 200 may store the analyte data in the memory 210 or a permanent storage device.

In step 530, the computer device 200 may calculate a calibration value to be used at current timing by using an artificial intelligence (AI) calibration model having analyte data measured by the analyte sensor and the stored analyte data as inputs. The AI calibration model, like the calibration value prediction model 321, may be trained to output a calibration value prediction value at current timing by using the analyte data measured by the analyte sensor and the analyte data measured by the reference device.

In step 540, the computer device 200 may compute the final analyte data by incorporating the calculated calibration value into the analyte data measured by the analyte sensor. The computed final analyte data may be transmitted and used by the connected device.

In some embodiments, step 530 and step 540 may be combined. For example, in step 530, the computer device 200 may output analyte data calibrated by using the AI calibration model having the analyte data measured by the analyte sensor and the stored analyte data as inputs. In this case, the AI calibration model may be trained to receive the analyte data measured by the analyte sensor and the stored analyte data as inputs and to output the calibrated analyte data. In this case, step 540 may be omitted.

Furthermore, in some embodiments, accumulated analyte data may be used as the analyte data measured by the analyte sensor. For example, data obtained by accumulating analyte data measured by the analyte sensor for a given time may be used as one of inputs to the AI calibration model. In other words, the computer device 200 may use (1) data obtained by accumulating analyte data measured by the analyte sensor for a given time and (2) stored analyte data as inputs to the AI calibration model.

As described above, a simple measurement difference at calibration timing is not used as a calibration value, but a result obtained by inputting the measurement difference to the calibration value prediction model is used as a calibration value through the AI calibration model. Accordingly, a calibration error according to the lapse of time can be reduced, and a calibration cycle can be increased.

Figure 6:
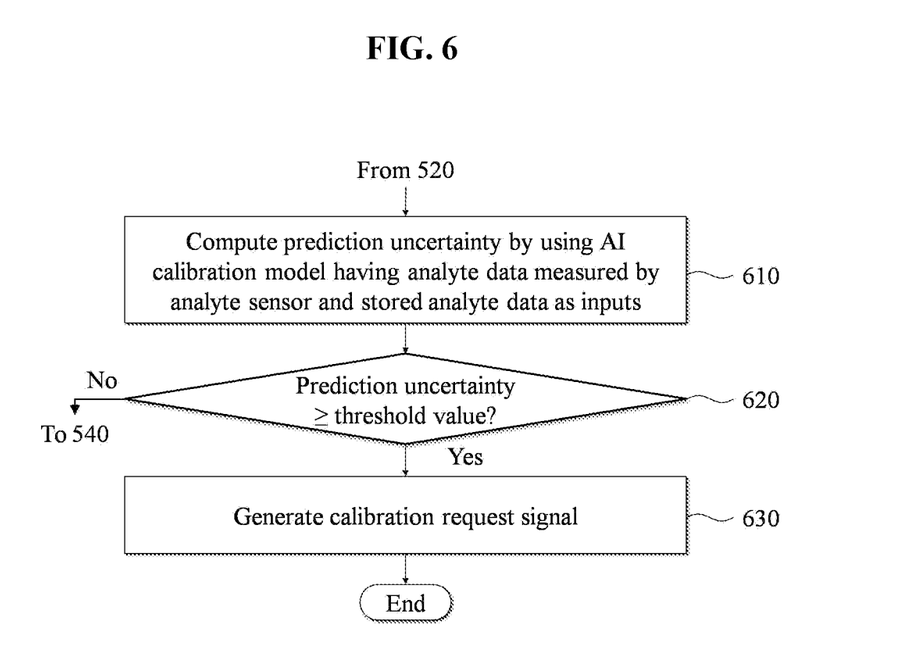
FIG. 6 is a flowchart illustrating an example of a method using prediction uncertainty in an embodiment of the present disclosure.

FIG. 6 is a flowchart illustrating an example of a method using prediction uncertainty in an embodiment of the present disclosure. Step 610 in FIG. 6 may be included in step 530 in FIG. 5. Steps 620 and 630 in FIG. 6 may be included between steps 530 and step 540 in FIG. 5. As will be described later, when step 630 is performed, step 540 may be omitted.

In step 610, the computer device 200 may compute prediction uncertainty by using the AI calibration model having analyte data measured by the analyte sensor and stored analyte data as inputs. For example, in some embodiments, in step 530, the computer device 200 may compute both a calibration value and prediction uncertainty by using the AI calibration model.

In step 620, the computer device 200 may determine whether the prediction uncertainty is equal to or greater than a preset threshold value. The computer device 200 may perform step 540 when the prediction uncertainty is smaller than the threshold value, and may perform step 630 when the prediction uncertainty is equal to or greater than the threshold value.

In step 630, the computer device 200 may generate a calibration request signal. In some embodiments, the generated calibration request signal may be transmitted to the connected device in order to request calibration. In other words, when the prediction uncertainty is smaller than the threshold value, the computer device 200 may use a calibration value without any change by performing step 540.

When the prediction uncertainty is equal to or greater than the threshold value, the computer device 200 may generate a calibration request signal and receive calibration data for calibration again by transmitting the calibration request signal. In this case, the calibration data may include analyte data measured by the reference device.

As described above, according to the embodiments of the present disclosure, a calibration error according to the lapse of time can be reduced and a calibration cycle can be increased because a simple measurement difference at calibration timing is not used as a calibration value, but a result obtained by inputting the measurement difference to the calibration value prediction model is used as a calibration value. Furthermore, the reliability of a currently predicted calibration value can be evaluated using the calibration value prediction model that outputs prediction uncertainty. Necessity for calibration can be determined based on the evaluation. Accordingly, unnecessary calibration can be avoided, and a user may be requested to immediately perform a calibration procedure regardless of a calibration cycle if calibration is necessary.

The aforementioned system or device may be implemented as a hardware component, a software component and/or a combination of a hardware component and a software component. For example, the device and components described in the embodiments may be implemented using one or more general-purpose computers or special-purpose computers, for example, a processor, a controller, an arithmetic logic unit (ALU), a digital signal processor, a microcomputer, a field programmable gate array (FPGA), a programmable logic unit (PLU), a microprocessor or any other device capable of executing or responding to an instruction. A processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary knowledge in the art may understand that the processing device may include a plurality of processing components and/or a plurality of types of processing components. For example, the processing device may include a plurality of processors or one processor and one controller. Furthermore, other processing configurations, such as a parallel processor, are also possible.

Software may include a computer program, a code, an instruction or a combination of one or more of them, and may configure a processor so that it operates as desired or may instruct processors independently or collectively. Software and/or data may be embodied in any type of a machine, component, physical device, virtual equipment, or computer storage medium or device so as to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file and a data structure alone or in combination. The program instructions stored in the medium may be specially designed and constructed for the present disclosure, or may be known and available to those skilled in the field of computer software. Examples of the computer-readable storage medium include magnetic media such as a hard disk, a floppy disk and a magnetic tape, optical media such as a CD-ROM and a DVD, magneto-optical media such as a floptical disk, and hardware devices specially configured to store and execute program instructions such as a ROM, a RAM, and a flash memory. Examples of the program instructions include not only machine language code that is constructed by a compiler but also high-level language code that can be executed by a computer using an interpreter or the like.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned components, such as the system, configuration, device, and circuit, are coupled or combined in a form different from that of the described method or replaced or substituted with other components or equivalents.

Accordingly, other implementations, other embodiments, and the equivalents of the claims fall within the scope of the claims.

The embodiments of the invention in which an exclusive property or privilege is claimed are defined as follows:

1. A method of calibrating, by a computer device comprising at least one processor, analyte data, the method comprising:
   receiving, by the at least one processor, first analyte data measured by a reference device;
   storing, by the at least one processor, the received first analyte;
   calculating, by the at least one processor, a calibration value by using an artificial intelligence (AI) calibration model having second analyte data measured by an analyte sensor and the stored first analyte data as inputs;
   calculating, by the at least one processor, final analyte data by incorporating the calculated calibration value into the second analyte data;
   increasing a calibration cycle based on the calculated calibration value;
   generating a calibration request signal in response to the calculated calibration value; and
   outputting the generated calibration request signal, regardless of the calibration cycle.

2. The method of claim 1, wherein calculating the calibration value comprises calculating, as the calibration value, an average of probability distributions of output nodes included in a neural network of the AI calibration model.

3. The method of claim 1, wherein calculating the calibration value comprises further computing prediction uncertainty for determining time when the first analyte data is received again by using the AI calibration model having the second analyte data and the stored first analyte data as inputs.

4. The method of claim 3, wherein the prediction uncertainty comprises dispersion of the probability distributions of the output nodes included in the neural network of the AI calibration model.

5. The method of claim 3, further comprising:
   comparing, by the at least one processor, the prediction uncertainty with a preset threshold value;
   generating, by the at least one processor, the calibration request signal when the prediction uncertainty is equal to or greater than the preset threshold value; and outputting, by the at least one processor, the generated calibration request signal.

6. The method of claim 5, wherein calculating the final analyte data comprises calculating the final analyte data when the prediction uncertainty is smaller than the preset threshold value.

7. The method of claim 5, wherein the calibration request signal comprises a signal for requesting re-measurement and re-reception of the first analyte data.

8. The method of claim 1, wherein the second analyte data comprises data obtained by accumulating analyte data measured by the analyte sensor for a given time.

9. A method of calibrating, by a computer device comprising at least one processor, analyte data, the method comprising:
  receiving, by the at least one processor, first analyte data measured by a reference device;
  storing, by the at least one processor, the received first analyte;
  calculating, by the at least one processor, calibrated second analyte data by using an artificial intelligence (AI) calibration model having second analyte data measured by an analyte sensor and the stored first analyte data as inputs;
  increasing a calibration cycle based on the calculated calibration value;
  generating a calibration request signal in response to the calculated calibration value; and
  outputting the generated calibration request signal, regardless of the calibration cycle.

10. A computer device comprising:
  at least one processor implemented to execute a computer-readable instruction,
  wherein the at least one processor is configured to:
  receive first analyte data measured by a reference device;
  store the received first analyte;
  calculate a calibration value by using an artificial intelligence (AI) calibration model having second analyte data measured by an analyte sensor and the stored first analyte data as inputs;
  calculate final analyte data by incorporating the calculated calibration value into the second analyte data;
  increase a calibration cycle based on the calculated calibration value;
  generate a calibration request signal in response to the calculated calibration value; and
  output the generated calibration request signal, regardless of the calibration cycle.

11. The computer device of claim 10, wherein in order to calculate the calibration value, the at least one processor calculates, as the calibration value, an average of probability distributions of output nodes included in a neural network of the AI calibration mode.

12. The computer device of claim 10, wherein in order to calculate the calibration value, the at least one processor further computes prediction uncertainty for determining time when the first analyte data is received again by using the AI calibration model having the second analyte data and the stored first analyte data as inputs.

13. The computer device of claim 12, wherein the prediction uncertainty comprises dispersion of the probability distributions of the output nodes included in the neural network of the AI calibration model.

14. The computer device of claim 12, wherein the at least one processor is configured to:
  compare the prediction uncertainty with a preset threshold value,
  generate the calibration request signal when the prediction uncertainty is equal to or greater than the preset threshold value, and
  output the generated calibration request signal.

* * * * *